(12) United States Patent
Shudo et al.

(10) Patent No.: US 10,004,710 B2
(45) Date of Patent: Jun. 26, 2018

(54) MEDICAMENT FOR THERAPEUTIC TREATMENT OF NEUROPATHIC DISEASE

(71) Applicant: KEMPHYS LTD., Tokyo (JP)

(72) Inventors: Koichi Shudo, Tokyo (JP); Kiyoshi Sugiyama, Tokyo (JP)

(73) Assignee: KEMPHYS LTD., Tokyo (JP)

( * ) Notice: Subject to any disclaimer, the term of this patent is extended or adjusted under 35 U.S.C. 154(b) by 6 days.

(21) Appl. No.: 14/442,519

(22) PCT Filed: Sep. 4, 2013

(86) PCT No.: PCT/JP2013/073784
§ 371 (c)(1),
(2) Date: May 13, 2015

(87) PCT Pub. No.: WO2014/112152
PCT Pub. Date: Jul. 24, 2014

(65) Prior Publication Data
US 2016/0256422 A1 Sep. 8, 2016

Related U.S. Application Data

(60) Provisional application No. 61/754,149, filed on Jan. 18, 2013.

(51) Int. Cl.
*A61K 31/195* (2006.01)
*A61K 31/197* (2006.01)
*A61K 47/10* (2017.01)
*A61K 9/00* (2006.01)
*A61K 9/08* (2006.01)

(52) U.S. Cl.
CPC .......... *A61K 31/197* (2013.01); *A61K 9/0014* (2013.01); *A61K 9/08* (2013.01); *A61K 31/195* (2013.01); *A61K 47/10* (2013.01)

(58) Field of Classification Search
CPC .................................................... A61K 31/197
USPC ......................................................... 514/561
See application file for complete search history.

(56) References Cited

U.S. PATENT DOCUMENTS 5,563,175 A * 10/1996 Silverman ............ A61K 31/197
514/561
6,211,171 B1 4/2001 Sawynok et al.
6,572,880 B2 6/2003 Murdock et al.
(Continued)

FOREIGN PATENT DOCUMENTS

CN 1891684 A * 1/2007
EP 0388306 1/1998
(Continued)

OTHER PUBLICATIONS

FDA Center for Drug Evaluation and Research, 2010, Application No. : 22-488, table 2. (https://www.accessdata.fda.gov/drugsatfda_docs/nda/2010/022488s000chemr.pdf ).*
(Continued)

*Primary Examiner* — Shengjun Wang
(74) *Attorney, Agent, or Firm* — Greenblum & Bernstein, P.L.C.

(57) ABSTRACT

A medicament to be applied as an external preparation for therapeutic treatment of a local symptom of a neuropathic disease, which contains gabapentin or pregabalin in the form of an aqueous solution.

7 Claims, 1 Drawing Sheet

(56) References Cited

U.S. PATENT DOCUMENTS

| | | | |
|---|---|---|---|
| 2004/0054005 A1* | 3/2004 | Lan | A61K 31/195 514/561 |
| 2004/0265364 A1 | 12/2004 | Ozturk et al. | |
| 2005/0059715 A1* | 3/2005 | Dooley | A61K 31/136 514/364 |
| 2005/0209319 A1* | 9/2005 | Cundy | A61K 31/22 514/484 |
| 2010/0184817 A1* | 7/2010 | Wolicki | A61K 31/24 514/401 |
| 2011/0065627 A1 | 3/2011 | Barathur et al. | |
| 2011/0178114 A1 | 7/2011 | Aung-Din | |
| 2011/0178177 A1 | 7/2011 | Wolicki et al. | |

FOREIGN PATENT DOCUMENTS

| | | |
|---|---|---|
| EP | 1940352 | 7/2008 |
| EP | 2316420 A1 * | 5/2011 |
| JP | 2006-511604 A | 4/2006 |
| JP | 2007-505097 | 3/2007 |
| JP | 2011-526889 | 10/2011 |
| WO | 98/03167 | 1/1998 |
| WO | 2005/089872 | 9/2005 |
| WO | 2007/049102 A1 | 5/2007 |
| WO | 2008/067991 | 6/2008 |
| WO | 2010/036937 A | 8/2010 |

OTHER PUBLICATIONS

Lyrica prescription information (FDA 2011 https://www.accessdata.fda.gov/drugsatfda_docs/label/2011/021446s026,022488s005lbl.pdf).*

Achrai et al., "Solubilization of Gabapentin into $H_{II}$ Mesophases", *The Journal of Physical Chemistry B*, vol. 115, No. 5, pp. 825-835, 2011.

Carlton et al., "Attenuation of Formalin-Induced Nociceptive Behaviors Following Local Peripheral Injection of Gabapentin", *Pain*, vol. 76, pp. 201-207, 1998.

"The History of Pluronic Lecithin Organogel: An Interview with Marty Jones, BSPHARM, FACA, FIACP", *International Journal of Pharmaceutical Compounding*, vol. 7, No. 3, pp. 180-183, 2003.

Gammaitoni et al., "Safety and Tolerability of the Lidocaine Patch 5%, a Targeted Peripheral Analgesic: A Review of the Literature", *J. Clin. Pharmacol.*, vol. 43, No. 2, pp. 111-117, 2003.

Plaza-Villegas et al., "Topical Pregabalin and Diclofenac for the Treatment of Neuropathic Orofacial Pain in Rats", *Oral Medicine*, vol. 114, No. 4, pp. 449-456, 2012.

International Search Report for Patent Application No. PCT/JP2013/073784, dated Nov. 5, 2013, along with an English language translation.

International Preliminary Report on Patentability for PCT/JP2013/073784, dated Jul. 30, 2015, along with an English language translation.

Japanese Office Action issued in JP Patent Application No. 2014-557316, dated Feb. 9, 2016, along with an English language translation.

European Search Report issued with respect to Application No. 13871380.5, dated Aug. 19, 2016.

Nurs. Today, Nov. 15, 2012, 27(6), pp. 59-63.

Sommer, M.; C.G. Bachman; K.M. Leibetanz; J. Schindehutte; T. Tings; W. Paulus, "Pregabalin in restless legs syndrome with and without neuropathic pain", Acta Neurologica Scandinavica, 2007, 115(5), pp. 347-350.

Japanese Office Action with English Translation for Japanese Application No. 2016-084901, dated May 23, 2017.

* cited by examiner

MEDICAMENT FOR THERAPEUTIC TREATMENT OF NEUROPATHIC DISEASE

CLAIM FOR PRIORITY

This application is a U.S. National Stage of PCT/JP2013/073784 filed on Sep. 4, 2013, and claims the priority benefit of U.S. provisional application 61/754,149, filed Jan. 18, 2013, the contents of which is expressly incorporated by reference herein in their entireties.

TECHNICAL FIELD

The present invention relates to a medicament for dermal application as an external preparation for therapeutic treatment of a neuropathic disease such as neuropathic pain.

BACKGROUND ART

Neuropathic pain consists of peripheral neuropathic pain and central neuropathic pain (U.S. Pat. No. 6,211,171). Various factors such as obstructions of various peripheral nerves, nerve root, spinal cord or a part of brain, infection of virus such as herpes virus (herpes zoster), and use of an anticancer agent induce variety of neuropathic pains such as allodynia, hyperalgesia, and prolonged response duration. Inflammations such as rheumatism and gout are also frequently accompanied by severe pain. Diabetic pain, post-herpes zoster pain, fiber muscle pain, and restless legs syndrome are also considered to be neuropathic diseases. Itch also has characteristics very similar to those of pain. Therapeutic treatments of these neuropathic diseases often encounters difficulty.

Gabapentin and pregabalin, which can be regarded as derivatives of gamma-aminobutyric acid (GABA), are used as an anti-epileptic that acts on the central nerve system, and they are also used for therapeutic treatments of pain or discomfort in the aforementioned neuropathic diseases (WO98/03167). Although the mode of action of these agents has not been fully elucidated, it is estimated that they bind with the $\alpha 2\delta$ subunit of the voltage-dependent-calcium channel to exhibit the efficacy (it is considered, however, that they do not act on the gaba receptor in the brain).

These agents are usually used as an oral agent, and when they are used for therapeutic treatment of pain, they are orally administered at a daily dose of 200 to 2,400 mg for gabapentin or 150 to 600 mg for pregabalin, or they sometimes may be administered at a still higher dose. Since these agents highly frequently cause side reactions concerning the central nerve system such as lethargy and vertigo even at a usual dose, as well as the case of using such high doses as mentioned above, these side reactions are most serious problems in the therapeutic treatment of pain.

For the therapeutic treatment of pain accompanying these diseases, besides a treatment based on systemic administration such as oral administration, a method of suppressing transfer of pain by local administration may also be contemplated. Pain is not necessarily felt equally in the whole body, and severe pain is locally felt in many cases. Therefore, when an analgesic effect can be attained by local administration, a therapeutic treatment can be realized with reduced side reactions by means of a lowered dose and the like. For example, local administration is effective in the therapeutic treatment of pain with a tricyclic compound antidepressant (U.S. Pat. No. 6,211,171), and a local anesthetic, of which typical example is lidocaine, is effective for therapeutic treatment of local pain. Local administration of a non-steroidal anti-inflammatory agent suppresses inflammation, and thereby ameliorates pain. Concerning local administration of these local anesthetics and the like, there are reports such as by Hind Harry (EP0388306), Gammaitoni et al. (J. Clin. Pharmaco., 2003, 43 (2), pp. 111-117).

An analgesic action may possibly be attained by local administration of pregabalin or gabapentin as an external preparation at a site of pain. However, in order to effectively attain an analgesic action with pregabalin or gabapentin, absorption of at least a certain amount of the drug is considered to be essential. Even if a percutaneous absorption system including various devices for the above purpose is used, a daily dose is limited. Moreover, if absorption is enhanced so as to obtain a high blood concentration, the same side reactions as those induced by oral administration will be induced. Although gabapentin and pregabalin are highly water-soluble, a water-soluble agent generally achieves poor percutaneous absorption, and is considered to be unsuitable for external use.

With regard to application of gabapentin to therapeutic treatment of neuropathic pain, Carlton et al. reported that subcutaneous administration of gabapentin was effective for suppressing pain in an animal model, and effective for the peripheral system (Pain, 1998, 76, pp. 201-207). There has been proposed a method of externally applying these agents in combination with other agents for analgesic purpose (EP1940352). For this administration scheme, various pharmaceutical compounds are exemplified for use in an aqueous preparation characterized by containing hydroxypropylmethylcellulose, and gabapentin and pregabalin are mentioned as mere examples among the various pharmaceutical compounds.

There is an example of use of a cetylated fatty acid ester as a percutaneous absorption enhancer (U.S. Patent Published Application No. 2011/0065627). As an example of pharmaceutical devising, it was reported that a preparation of pregabalin (and combination of pregabalin and diclofenac, International Journal of Pharmaceutical Compounding, 2003, 7, pp. 180-183) suppressed pain due to neuropathic orofacial pain in rats, and the infraoebital nerve territory in the vibrissae area was chosen as the administration site in order to obtain a higher blood concentration (Oral Medicine, 2012, 114, pp. 449-456). U.S. Pat. No. 6,572,880 (Murdock) disclosed that administration of a pharmaceutical preparation obtained in the presence of propylene glycol and soybean lecithin using a Luer Loc syringe provided remission of spastic tetraplegia induced by traumatic injury over one week. International Patent Publication WO2008/067991 reported that an amine compound formed a complex with an acrylic acid polymer to generally increase absorption of the agent, and gabapentin is mentioned as an example of such agent. Cundy et al. devised a percutaneous absorption system to develop an external preparation of a prodrug of gabapentin or pregabalin (International Patent Publication WO2005/089872).

PRIOR ART REFERENCES

Patent Documents

Patent document 1: U.S. Pat. No. 6,211,171
Patent document 2: International Patent Publication WO98/03167
Patent document 3: European Patent No. 0388306
Patent document 4: U.S. Patent Published Application No. 2011/0065627
Patent document 5: U.S. Pat. No. 6,572,880

Patent document 6: International Patent Publication WO2008/067991
Patent document 7: International Patent Publication WO2005/089872
Patent document 8: European Patent No. 1940352

Non-Patent Documents

Non-patent document 1: J. Min. Pharmaco., 2003, 43(2), pp. 111-117
Non-patent document 2: Pain, 1998, 76, pp. 201-207
Non-patent document 3: International Journal of Pharmaceutical Compounding, 2003, 7, pp. 180-183
Non-patent document 4: Oral Medicine, 2012, 114, pp. 449-456

DISCLOSURE OF THE INVENTION

Object to be Achieved by the Invention

An object of the present invention is to provide a means for therapeutic treatment or amelioration of pain or discomfort such as itch in a neuropathic disease such as neuropathic pain, wherein external application is chosen as the route of administration.

Means for Achieving the Object

The inventor of the present invention conducted various researches to achieve the aforementioned object. As a result, it was surprisingly found that, by applying gabapentin or pregabalin in the form of an aqueous solution as an external preparation, pain or discomfort such as itch induced by a neuropathic disease such as neuropathic pain was successfully and dramatically ameliorated without employing any means especially for enhancing percutaneous absorption.

The present invention thus provides a medicament to be applied as an external preparation for therapeutic treatment of a local symptom of a neuropathic disease, which contains gabapentin or pregabalin in the form of an aqueous solution. The medicament of the present invention is a medicament in the form of an aqueous solution that contains no ingredient for promoting percutaneous absorption of gabapentin or pregabalin.

According to a preferred embodiment of the present invention, there are provided the aforementioned medicament, wherein the local symptom is pain or itch, and the aforementioned medicament, wherein the neuropathic disease is neuropathic pain. According to another preferred embodiment of the present invention, the medicament of the present invention may contain an organic solvent miscible with water, for example, ethanol and the like.

As another aspect of the present invention, there is provided use of gabapentin or pregabalin for manufacture of a medicament in the form of an aqueous solution to be applied as an external preparation for therapeutic treatment of a local symptom of a neuropathic disease.

As still another aspect of the present invention, there is provided a method for therapeutic treatment of a local symptom of a neuropathic disease, which comprises the step of locally applying gabapentin or pregabalin in the form of an aqueous solution as an external preparation.

Effect of the Invention

According to the present invention, with an aqueous solution of gabapentin or pregabalin which is the simplest form as a pharmaceutical preparation, local pain or discomfort such as itch induced by a neuropathic disease such as neuropathic pain can be surprisingly and dramatically ameliorated. According to the present invention, an extremely strong local action of gabapentin or pregabalin can be attained only by topically applying an aqueous solution of gabapentin or pregabalin to a local lesion without using any ingredient for promoting percutaneous absorption of gabapentin or pregabalin. Moreover, a dose can be decreased to about 1/10 of the dose used for oral administration. Accordingly, expression of side reactions can be avoided, and further, the medicament is also advantageous from an economical point of view.

MODES FOR CARRYING OUT THE INVENTION

Figure 1:
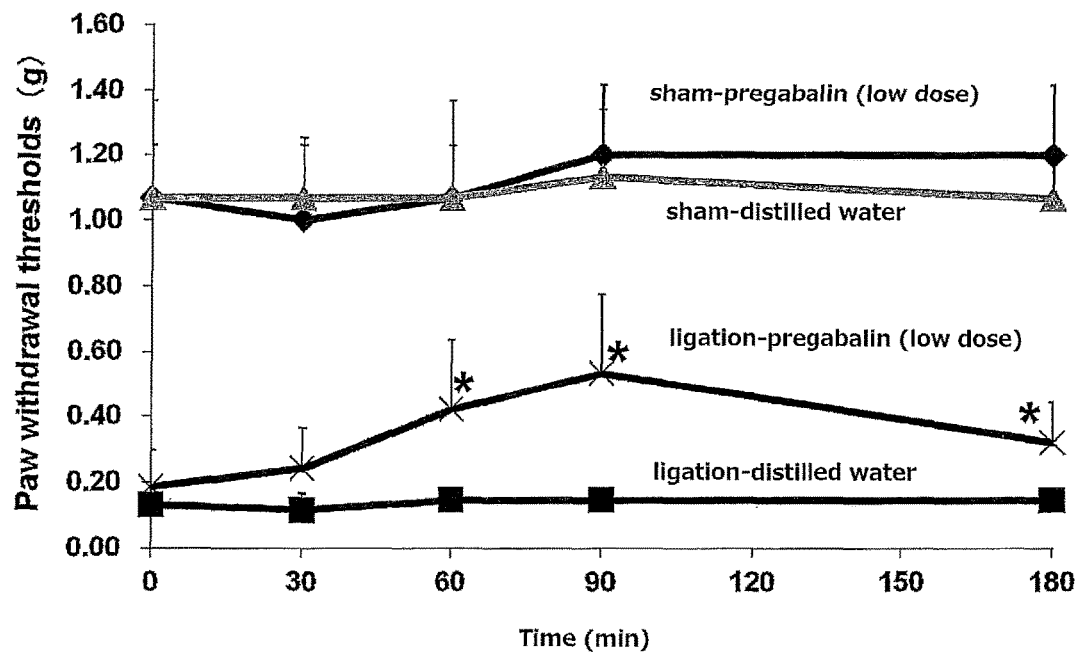
FIG. 1 is a graph showing results of measurement of analgesic effect obtained by applying an aqueous solution of pregabalin (2.5 mg/ml) to a neuropathic pain mouse. The asterisks (*) indicate the presence of a significant difference with respect to the distilled water-applied group.

The medicament of the present invention is in the form of an aqueous solution to be applied to the skin as an external preparation which contains gabapentin or pregabalin as an active ingredient, and is characterized by not containing any ingredient for promoting percutaneous absorption of gabapentin or pregabalin.

A concentration of gabapentin or pregabalin in the aqueous solution may be, for example, about 1 to 50 mg/ml. As water, pure water, purified water, ion-exchanged water, tap water, distilled water, and the like can be used. When tap water or the like is used, small amounts of chlorine, metal ions such as calcium ion and magnesium ion, and the like, may be contained.

Although pH of the aqueous solution of gabapentin or pregabalin is not particularly limited, pH may be, for example, about 5.5 to 8.5, preferably about 5.5 to 7.3. Although pH of the aqueous solution can be adjusted as required by using a pharmaceutically acceptable buffer, an α-amino acid or a salt thereof, or the like, the means for adjusting pH is not limited to these examples.

The aqueous solution of gabapentin or pregabalin may contain additives, for example, antimicrobial and antifungal agents such as sodium sorbate and ethylparaben, perfumes, colorants, stabilizers such as anti-oxidants, and the like, as well as natural or synthetic thickeners such as small amounts of sodium hyaluronate, carboxymethylcellulose sodium, polyvinylpyrrolidone, polyoxyethylene/polyoxypropylene copolymer, sodium salt of water-soluble acrylate polymer or water-soluble methacrylate/maleate copolymer, and the like for ease of handling of the aqueous solution, as required. The thickeners are used for increasing viscosity, and the aqueous solution containing a thickener is a preferred embodiment of the aqueous solution of the present invention. The medicament of the present invention may also be provided in the form of an aqueous solution or an aqueous solution having an appropriate adhering strength applied on a support such as nonwoven fabric, of which surface is covered with a liner such as a polyethylene film. Also in these cases, no absorption enhancer is necessary. Specific examples of the preparation form using the aqueous solution of the present invention include aqueous solution, spray, mist, foam, plaster, emulsion, lotion, patch, syrup, gargle, and the like.

The aqueous solution of gabapentin or pregabalin may contain an organic solvent miscible with water such as ethanol, isopropanol, and ethylene glycol, as required. As the organic solvent miscible with water, ethanol is preferred. Although content of the organic solvent is not particularly limited, it is, for example, 50% or less, preferably 30% or less, more preferably 10% or less, particularly preferably 1% or less, based on the total volume of the solution.

The aqueous solution of gabapentin or pregabalin can be prepared beforehand, aseptically filled in a container, stored, distributed, and then clinically used. However, it is also possible to use gabapentin or pregabalin by dissolving gabapentin or pregabalin in the form of solid in water upon use, preferably immediately before application to the skin. The latter embodiment is preferred, because bacterial contamination is avoidable, and therefore it is generally unnecessary to add antibacterial and antifungal agent and the like in the aqueous solution. Although it is preferred that gabapentin or pregabalin is completely dissolved in the aqueous solution, the solution may be in the form of a suspension where a part of gabapentin or pregabalin remains undissolved. Such an embodiment is also encompassed within the "aqueous solution" referred to in this specification. Further, the medicament of the present invention may also be provided as a medicament consisting of a combination of gabapentin or pregabalin and an aqueous medium for dissolution for preparing the aqueous solution as a kit.

Examples of the neuropathic disease as an object of the application of the medicament of the present invention include, for example, neuropathic pain, but it can also be applied to diabetic pain, post-herpes zoster pain, fiber muscle pain, and the like. The object of the application is not limited to pain, and it can be used for, as various peripheral neuropathic pains and central neuropathic pains, painful diabetic neuropathy, complex regional pain syndrome, nerve damage induced by chemotherapy, cancer pain, HIV-associated sensory neuropathy, HIV-associated myelopathy, phantom limb pain, trigeminal neuralgia, sciatic neuralgia, orofacial pain, acute or chronic inflammatory demyelinating polyradiculopathy, alcoholic neuropathy, carpal tunnel syndrome, knuckle pain, snapping finger, iatrogenic nerve damage, neurothlipsia by tumor or nerve damage by infiltration, post radiation nerve damage, toxic peripheral neuropathy, post-traumatic peripheral nerve injury pain, glossopharyngeal neuralgia, autoimmune nerve damage, acute, chronic or intractable muscle and fascia pain, postapoplectic pain, post-traumatic spinal cord injury pain, pain accompanying multiple sclerosis or Parkinson's disease, spinal canal stenosis or hernia pain, so-called low back pain, pain resulting from cervical spondylosis or ligamentum osteosis, pain of stomatitis, perishoulder arthritis, rheumatoid arthritis or osteoarthritis, nociceptive pain, pain of incised wound, abrasion, bone fracture, or bruise, pain caused by insertion of dialysis needle or pain resulting from dialysis at the time of dialysis, senile or nervous itch, itch of scalp, atopic dermatitis, restless legs syndrome, numbness of hand and foot, pain after odontectomy, postoperative pain, pain prophylaxis by preoperative administration, and the like. Furthermore, it can also be used for ameliorating itch of acute local allergies induced by bug bite or the like.

Although the mode of using the medicament of the present invention is not particularly limited, an aqueous solution of gabapentin or pregabalin can usually be directly and topically applied to the skin of a lesion site of a neuropathic disease, and air-dried. After the topical application, moisture shortly evaporates, and gabapentin or pregabalin as the active ingredient remains on the surface of the skin. After evaporation of moisture, pregabalin or gabapentin is retained on the surface of the skin in contact with the skin in the form of a solid or film in a microcrystalline or amorphous state, or a solid of a moistened state containing moisture that does not evaporate but remains therein, or the like. Although an amount of the aqueous solution for topical application is not particularly limited, the amount may be, for example, about 0.1 to 3 ml/100 $cm^2$, and the amount of the active ingredient per square centimeter may be 1 to 1,000 μg. After the aqueous solution is applied and dried, the application may be repeated to increase dose for a specific site, and it is thereby made possible to apply the active ingredient at a high concentration to a specific painful point of, for example, fiber muscle pain. Wettability can be maintained by adding a thickener. Moreover, by increasing the amount of the thickener and the content of the active ingredient, the efficacy may be maintained over a longer period of time.

EXAMPLES

Hereafter, the present invention will be still more specifically explained with reference to examples. However, the scope of the present invention is not limited by the following examples.

Example 1

Pregabalin (75 mg) was dissolved in distilled water (3 ml). This aqueous solution was applied mainly on the skin of the upper arm part of the right arm and dried, which part was a lesion of neuropathic pain of the right arm (especially upper arm part) diagnosed to be resulting from cervical spondylosis. The aqueous solution was applicable over the whole arm (about 500 $cm^2$) with a volume of 3 ml. The grade of the pain was 7 (according to ten-point scale, it imposes serious obstruction of sleep). The pain was markedly ameliorated after about 30 minutes (grade 3 or 4), the analgesic action continued over 6 hours or more, and thus sufficient sleep was attained.

Example 2

To a patient (male, 73 years old), feeling oppressive pain in both lower extremities, especially calves, and complaining pain significantly obstructing walking, the aqueous solution of Example 1 (1 ml) was applied to one leg suffering from severer pain. After about 30 minutes, feeling of remission was obtained, and after 12 hours, the pain was clearly suppressed. After 3 days, the pain markedly decreased, and a remarkable effect was positively obtained as compared with the lower extremity not applied with the aqueous solution. On the fourth day, administration was started for the leg that had not been applied with the aqueous solution. On the third day, the pain was ameliorated similarly to the leg that received the precedent administration of the aqueous solution. Rebound of pain after the administration was not observed.

Example 3: Test Example in Low Back Pain Patient (Female, 64 Years Old) Diagnosed as Intervertebral Disc Herniation of Fifth Lumbar Vertebra Pregabalin was administered to a patient who became impossible to walk due to intense pain of the waist, and simultaneously suffering from numbness from the tips to around the roots of pedal fingers.

January 8: Although nerve blocking was performed, the pain remained unchanged.

January 15: Pregabalin (Lyrica), Cerecox, and Gaster were prescribed. Taking of Lyrica (oral administration) was stopped after two days for intense vertigo and nausea according to self-diagnosis of the patient. The intense pain and numbness continued until the beginning of February.

February 28: An external preparation of pregabalin (the aqueous solution of Example 1 supplemented with 0.1% hyaluronic acid) was applied to the sites of pain <waist, thigh, and back of leg> twice a day in a volume of 2 ml each. After the third day, the patient felt no pain about 30 minutes to 1 hour after the application. However, a condition continued for about one month in that, when the preparation was applied in the morning, the patient felt pain in the afternoon.

April 22: The period of time where the patient was not annoyed by the pain became prolonged, and when the patient had everyday life, the patient felt pain from around the evening, but the pain was not intense. Numbness continued.

May 27: The external application was terminated. During the application period, the patient did not feel unsteadiness, and the skin did not become red.

Example 4

An aqueous solution was prepared in the same manner as in Example 1 except that an isotonic solution of sodium chloride was used instead of the distilled water used in Example 1.

Example 5

An aqueous solution was prepared in the same manner as in Example 1 except that a mixture of distilled water and ethanol (mixing ratio=9:1) was used instead of the distilled water used in Example 1.

Example 6

An aqueous solution was prepared in the same manner as in Example 1 except that gabapentin (75 mg) was used instead of pregabalin used in Example 1.

Example 7

Pregabalin (75 mg) was dissolved in distilled water (warm water, 2 ml), and this aqueous solution was added with 0.25% aqueous sodium hyaluronate (1 ml) to prepare an aqueous solution (about 3 ml).

Example 8

An aqueous solution of about pH 5.5 was prepared by adding an acetate buffer to the aqueous solution prepared in Example 1.

Example 9

An aqueous solution of pH 8.7 was prepared by adding a sodium acetate solution to the aqueous solution prepared in Example 1.

Example 10

An aqueous solution was prepared by adding 0.1% ethylparaben to the aqueous solution prepared in Example 1 and dissolving.

Example 11

Sodium polyacrylate (sodium polyacrylate HAS, 1.0%, 10 ml, NIPPON SHOKUBAI) was added with a pregabalin aqueous solution (10 ml) prepared in the same manner as that of Example 1. The preparation obtained can be applied to diseased parts without any further treatment. Further, a 10% sodium polyacrylate solution was added with the aqueous solution prepared in Example 1 (20 ml), and the mixture was sufficiently stirred, and defoamed by using a conditioning mixer (trade name, Awatori Neritaro; Thinky) The preparation obtained was applied and extended on one side of polyester nonwoven fabric (trade name, Plaster Base Materials; Japan Vilene) in a thickness of 2 mm, moisture was appropriately evaporated, then the applied surface was covered with a nylon film, and the resulting plaster was cut into a size of 100 mm×50 mm.

Example 12

An aqueous solution containing pregabalin (150 mg) was applied to the back of an adult (male, 73 years old). After the application, blood was collected, and the serum was deproteinized, and then reacted with dinitrobenzenesulfonyl chloride to derivatize pregabalin. Pregabalin was quantified by LC/MS. The pregabalin concentration reached 9 ng/ml 30 minutes after the administration, and this concentration was maintained thereafter over 3 hours or longer.

Example 13: Suppression of Allodynia Pain in Mouse Nerve Ligation Model

Figure 2:
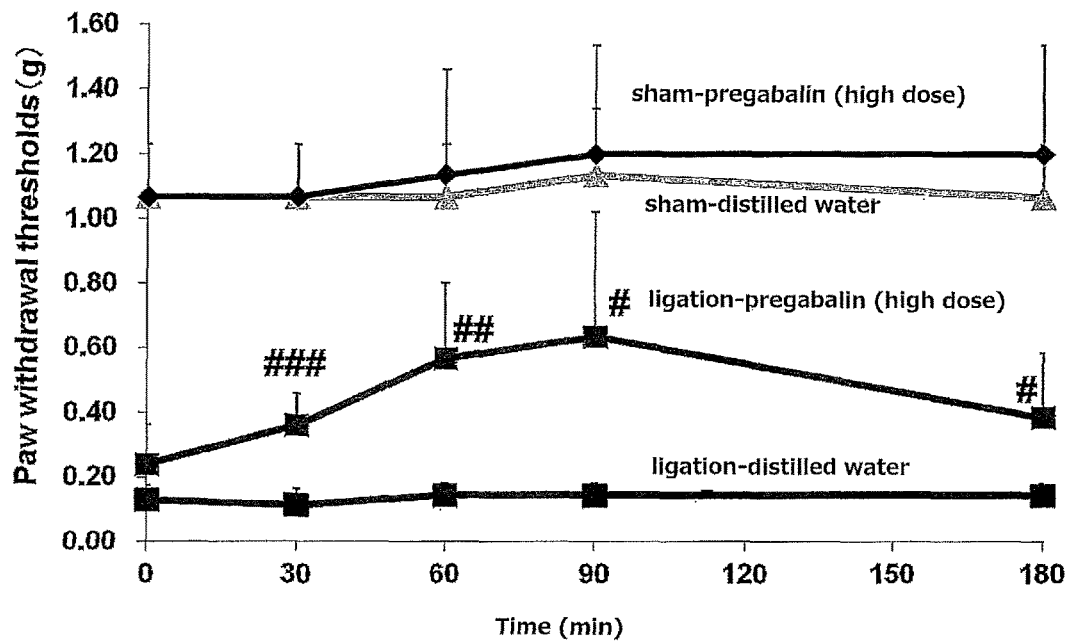
FIG. 2 is a graph showing results of measurement of analgesic effect obtained by applying an aqueous solution of pregabalin (7.5 mg/ml) to a neuropathic pain mouse. The asterisks (*) indicate the presence of a significant difference with respect to the distilled water-applied group.

The nerves L5 and L6 of mice (n=6) were ligated with silk threads to prepare pain model. A sham group was prepared as a control (n=6). After 4 weeks, hind legs of the mice were immersed in a 2.5 mg/ml or 7.5 mg/ml aqueous solution of pregabalin (solution prepared by dissolving 75 mg of pregabalin in 10 ml or 30 ml of distilled water) 5 minutes before the measurement until the hair of whole right hind leg was wetted with the solution, and air-dried over 30 minutes after the application. In this state, pain threshold was measured by using a von Frey standard filament, and then pain threshold was measured in the same manner 60 minutes, 90 minutes, and 180 minutes thereafter. For both the pregabalin low dose group and high dose group, statistically significant improvement was observed in the pain threshold of the nerve-ligated group compared with the medium solvent-applied group (FIGS. 1 and 2), and this effect was maintained even after 3 hours.

Example 13

A rat pain test was performed in a model according to the method of Seltzer (Seltzer, Pain, 1990, 43, pp. 205-218). More specifically, the skin of the left femoral region of a rat was cut under anesthesia attained by inhalation of 2% isoflurane to expose the sciatic nerve, ½ to ⅓ of the nerve was ligated with silk threads (8-0), and the muscular tunics were sutured at one or two sites. Fourteen days after the preparation of the model, pain threshold values of the right and left footpads were measured. For the measurement, a von Frey filament was used, and the pain threshold values were obtained by the up-and-down method. Pregabalin was dissolved at a concentration of 10.0 mg/mL in water containing 0.1% Tween 80, and 0.10 mL of the solution was applied to the footpads of both legs 17 days after the preparation of the model. The pain threshold values (g) of the left and right footpads were measured 1, 3, and 5 hours afterward. Sufficient increase of the threshold values was observed for the pain model legs after 1 hour. The results for the model leg (left) are shown in Table 1, and the results for the normal leg (right) are shown in Table 2. Increase of the threshold value was also observed for the normal leg.

TABLE 1

Test group: Pregabalin 1 mg/site (model site)

| Animal No. | Before administration | 1 Hour after administration | 3 Hour after administration | 6 Hour after administration |
|---|---|---|---|---|
| 71 | 1.4 | 6.0 | 4.0 | 2.0 |
| 72 | 1.4 | 6.0 | 4.0 | 2.0 |
| 73 | 1.4 | 6.0 | 4.0 | 2.0 |
| 74 | 2.0 | 8.0 | 6.0 | 4.0 |
| 75 | 1.4 | 2.0 | 2.0 | 1.0 |
| 76 | 1.4 | 6.0 | 6.0 | 1.0 |
| 77 | 1.4 | 6.0 | 2.0 | 2.0 |
| 78 | 2.0 | 4.0 | 4.0 | 1.0 |
| Average | 1.6 | 5.5 | 4.0 | 1.9 |
| S.E. | 0.1 | 0.6 | 0.5 | 0.4 |

TABLE 2

Test group: Pregabalin 1 mg/site (normal site)

| Animal No. | Before administration | 1 Hour after administration | 3 Hour after administration | 6 Hour after administration |
|---|---|---|---|---|
| 71 | 10.0 | 26.0 | 10.0 | 15.0 |
| 72 | 10.0 | 26.0 | 15.0 | 15.0 |
| 73 | 15.0 | 26.0 | 15.0 | 10.0 |
| 74 | 8.0 | 10.0 | 10.0 | 10.0 |
| 75 | 8.0 | 8.0 | 10.0 | 8.0 |
| 76 | 10.0 | 15.0 | 26.0 | 10.0 |

TABLE 2-continued

Test group: Pregabalin 1 mg/site (normal site)

| Animal No. | Before administration | 1 Hour after administration | 3 Hour after administration | 6 Hour after administration |
|---|---|---|---|---|
| 77 | 10.0 | 15.0 | 15.0 | 10.0 |
| 78 | 15.0 | 26.0 | 26.0 | 10.0 |
| Average | 10.8 | 19.0 | 15.9 | 11.0 |
| S.E. | 1.0 | 2.8 | 2.4 | 0.9 |

INDUSTRIAL APPLICABILITY

According to the present invention, local pain or discomfort such as itch induced by a neuropathic disease such as neuropathic pain can be dramatically reduced with an aqueous solution of gabapentin or pregabalin, which is the simplest preparation form.

What is claimed is:

1. A method for therapeutic treatment of a local symptom of a neuropathic disease, which comprises topically applying to the skin pregabalin as the sole ingredient for the therapeutic treatment of the local symptom of a neuropathic disease, in the form of an aqueous solution as an external preparation, the aqueous solution containing 1 to 50 mg/ml of pregabalin, and wherein the external preparation contains no ingredient promoting percutaneous absorption of the pregabalin, and contains no ethanol.

2. The method according to claim 1, wherein the local symptom is pain or itch.

3. The method according to claim 1, wherein the neuropathic disease is neuropathic pain.

4. The method according to claim 2, wherein the neuropathic disease is neuropathic pain.

5. The method according to claim 1, further comprising at least one additive.

6. The method according to claim 5, wherein the additive is selected from antimicrobial agents, antifungal agents, and thickeners.

7. The method according to claim 5, wherein the additive is a sorbate or a paraben for preventing microbial and/or fungal growth in the medicament.

* * * * *